United States Patent [19]

Yavitz et al.

[11] Patent Number: 5,795,343
[45] Date of Patent: Aug. 18, 1998

[54] ANTISEPTIC APPLICATOR DEVICE

[76] Inventors: Edward Q. Yavitz, 3828 Spring Creek Rd., Rockford, Ill. 61114; Randall S. Yavitz, 27 W. Morten Ave., Phoenix, Ariz. 85021

[21] Appl. No.: 851,744

[22] Filed: May 6, 1997

[51] Int. Cl.$^6$ .................................................. A61M 35/00
[52] U.S. Cl. ............................ 604/310; 604/1; 604/289
[58] Field of Search .............................. 604/1–3, 289, 604/290, 304, 306, 310; 602/48, 53; 206/828

[56] References Cited

U.S. PATENT DOCUMENTS 1,822,567  9/1931  Davies ........................................ 604/1
4,765,478  8/1988  Bringloe .................................. 604/290

*Primary Examiner*—John G. Weiss
*Assistant Examiner*—Dennis Ruhl
*Attorney, Agent, or Firm*—Robert A. Van Someren

[57] ABSTRACT

A device is designed for easy application of an antiseptic, such as peroxide, to an injured area. The device includes a housing having a central cavity in which an absorbent pad, such as a sponge, is permanently affixed. An antiseptic, e.g. peroxide, is also disposed within the cavity and absorbed by the pad. A flexible cover is sealed to the housing to close the cavity and contain the absorbent pad and the antiseptic. The cover is designed for easy removal to expose the pad and its absorbed antiseptic.

20 Claims, 3 Drawing Sheets

ANTISEPTIC APPLICATOR DEVICE

FIELD OF THE INVENTION

The present invention relates generally to an applicator for applying antiseptic, such as peroxide, to an area of injury, and particularly to a hand held unit with a sponge affixed thereto that is easy for children to grasp and use.

BACKGROUND OF THE INVENTION

Antiseptics are commonly used in the treatment of various injuries, such as cuts and abrasions. For example, rubbing alcohol or peroxide is applied to a person's injury to kill bacteria and reduce the chance of infection. Typically, a cotton swab is soaked with antiseptic that must be poured from a bottle or other container. This process can be somewhat awkward and difficult to implement, particularly by children. However, children are often the ones most susceptible to cuts, scrapes and other injuries. Therefore, it would be advantageous to have an easy-to-use single application package that allowed a person, such as a child, to readily apply antiseptic to the injured area.

SUMMARY OF THE INVENTION

The present invention features a device for applying antiseptic to an area of injury. The device includes a housing having a cavity and a rim extending along the periphery of the cavity. An absorbent pad, such as a sponge is attached to the housing and disposed within the cavity. An antiseptic is also disposed within the cavity in contact with the absorbent pad. A cover is sealed to the rim to contain the absorbent pad and the antiseptic within the cavity. The cover is designed so that it may be pulled back easily by a child to expose the absorbent pad for use in applying the antiseptic to a desired area. Preferably, the absorbent pad is compressed within the cavity so that upon removal of the cover, the pad expands outwardly beyond the rim to facilitate application of the antiseptic. Additionally, the housing is designed for easy grasping by a child.

According to another aspect of the invention, the device includes a housing having a bottom wall and a side wall extending therefrom to form a cavity. The side wall terminates at a rim opposite the bottom wall. A pad and an antiseptic liquid are disposed within the cavity. A flexible cover is sealed by, for instance, an adhesive or heat sealing to the rim to retain the antiseptic fluid within the cavity prior to use.

According to yet another aspect of the invention, the device is designed for applying various medications to a desired area. The device includes a housing having a cavity and a pad disposed within the cavity. The pad is held within the cavity so that it will not become separated from the housing during normal usage. A medicinal substance is disposed in contact with the pad and a cover is attached to the housing to enclose the cavity. The cover may simply be pulled back to expose the pad and the medicinal substance for application to the desired area.

BRIEF DESCRIPTION OF THE DRAWINGS

The invention will hereafter be described with reference to the accompanying drawings, wherein like reference numerals denote like elements, and.

DETAILED DESCRIPTION OF THE PREFERRED EMBODIMENTS

Figure 1:
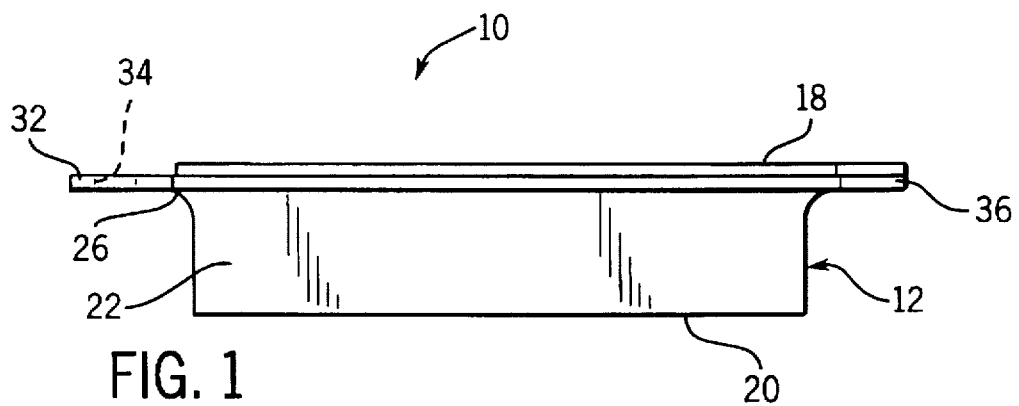
FIG. 1 is a side view of a device according to a preferred embodiment of the present invention.
Figure 2:
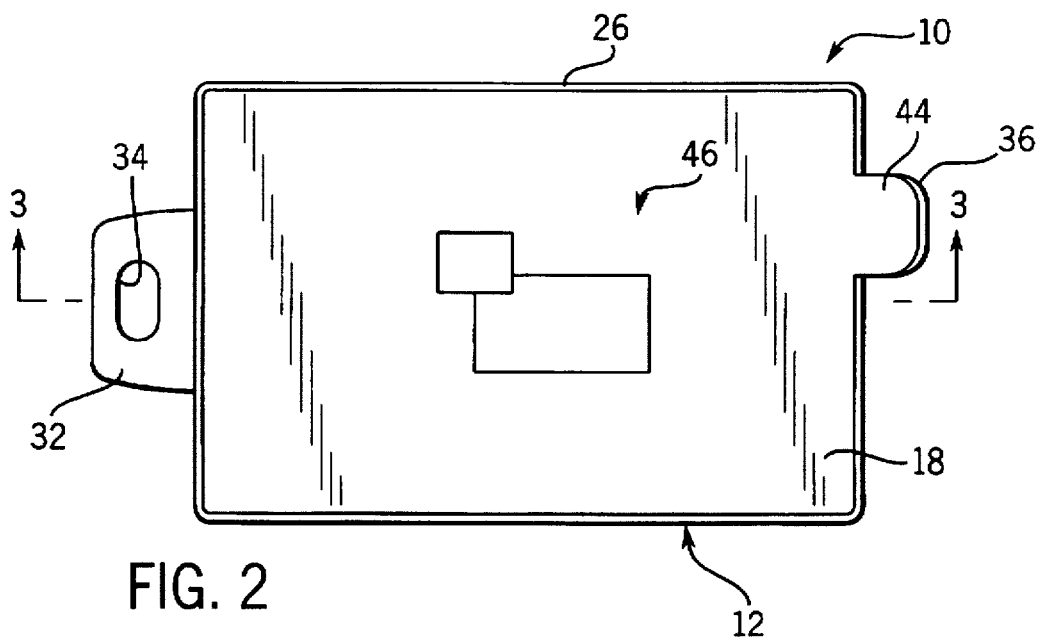
FIG. 2 is a top of the device illustrated in FIG. 1.
Figure 3:
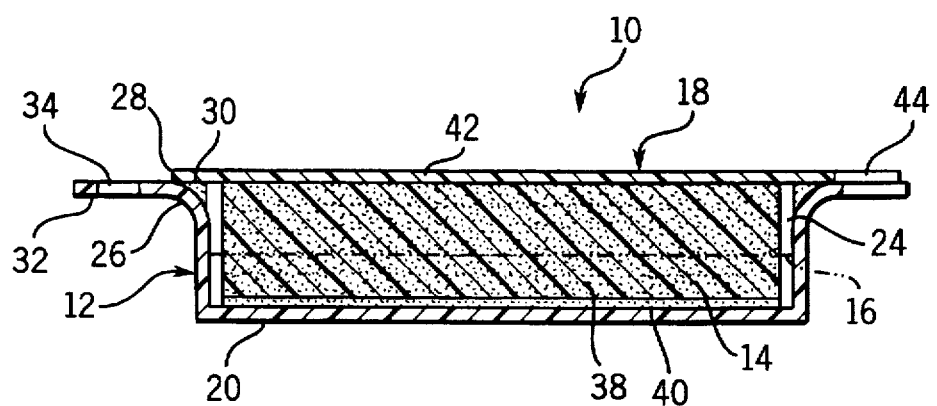
FIG. 3 is a cross-sectional view of the device taken generally along line 3—3 of FIG. 2.

Referring generally to FIGS. 1–3, a device 10 for applying medication, such as antiseptic, is illustrated according to a preferred embodiment of the present invention. Device 10 includes a housing 12, an applicator element 14, a medicinal substance 16, such as an antiseptic, and a cover 18.

In the preferred embodiment, housing 12 includes a bottom wall 20 and a side wall 22 extending therefrom in a direction generally transverse to bottom wall 20. Bottom wall 20 and side wall 22 cooperate to form a cavity 24 within housing 12 as best illustrated in FIG. 3. Bottom wall 20 and side wall 22 can be constructed and combined in a variety of ways to create cavities of various shapes. In the illustrated embodiment, side wall 22 is constructed with four walls or wall sections to form cavity 24 with a rectangular shape.

Side wall 22 preferably terminates at a rim 26 that extends about the periphery of side wall 22 of housing 12. Rim 26 includes a mounting surface 28. Mounting surface 28 may be designed to permit attachment of cover 18 by, for instance, an adhesive 30 or heat sealing when cover 18 is attached to housing 12.

Optionally, housing 12 may include a tab 32 having an opening 34 therethrough to allow device 10 to be hung on a conventional display. Tab 32 may be attached or integrally molded with housing 12. For example, it may extend outwardly from rim 26 as illustrated. Additionally, housing 12 may include an extension 36 that also is attached or integrally molded with housing 12 such that it extends from rim 26. Extension 36 is designed to cooperate with cover 18 to facilitate the pulling away of cover 18 from housing 12. Housing 12, including extension 36 and tab 32 can be made from a variety of materials, but it is preferred that they are all formed from a plastic material, such as injection moldable plastic.

Applicator element 14 is preferably a pad able to absorb medicinal substance 16. The pad is held affixed within cavity 24 SO that it does not become dislodged from cavity 24 during application of medicinal substance 16 to a desired area. In other words, housing 12 effectively provides an easy to grasp handle to aide in the application of medicinal substance 16 via applicator element 14. For some applications, it is desirable that applicator element 14 be compressed between cover 18 and bottom wall 20. Thus, upon separation of cover 18 from housing 12, applicator element 14 expands to extend above or beyond rim 26 (see FIG. 5). This facilitates the process of applying medicinal substance 16 to an area of injury.

In the most preferred embodiment, applicator element 14 is a pad that comprises a sponge 38. Sponge 38 is readily compressible between cover 18 and bottom wall 20, and it is also able to absorb medicinal substance 16, particularly when medicinal substance 16 is in the desired liquid form.

The applicator element, such as sponge 38, can be held within cavity 24 in a variety of ways, such as press fitting, heat sealing, or adhering sponge 38 to housing 12. In the preferred embodiment as illustrated in FIG. 3, sponge 38 is adhered to housing 12 at bottom wall 20 by an adhesive layer 40.

Medicinal substance 16 can include differing substances in a variety of forms. When applicator element 14 is an absorbent pad, such as sponge 38, it is preferred that medicinal substance 16 be in a liquid form to facilitate absorption of the medicinal substance 16 throughout sponge 38. Preferably, medicinal substance 16 is an antiseptic, such as peroxide, which permits a person, such as a child, to use device 10 in the treatment of cuts, abrasions and other injuries to kill bacteria and prevent infection.

In the preferred embodiment, cover 18 comprises a flexible sheet 42 that is adhered or heat sealed to mounting surface 28 of housing 12 to close cavity 24 and seal applicator element 14 along with medicinal substance 16 within cavity 24. Flexible sheet 42 may also include a pull tab 44 that lies over extension 36 when cover 18 is closed over cavity 24. Pull tab 44 is not adhered to extension 36. This facilitates grasping of pull tab 44 by a user when cover 18 is pulled back from housing 12 to expose applicator element 14 and medicinal substance 16. (See FIGS. 4 and 5.)

Cover 18 also includes a display area 46 (see FIG. 2) for carrying logos, information, cartoon characters, designs, etc. Display area 46 can be used for placement of a visually entertaining design or character that renders use of device 10 more acceptable and enjoyable for children. This encourages children to use device 10 for treating cuts and abrasions rather than fearing the application of antiseptic to injured areas.

Figure 4:
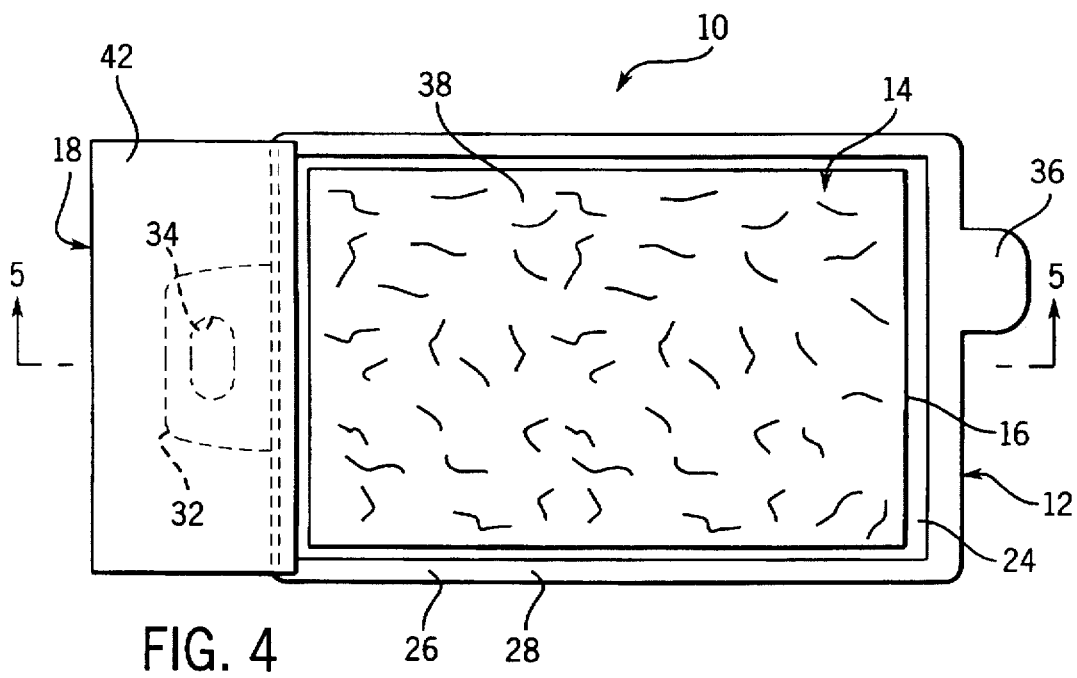
FIG. 4 is a top view of the device illustrated in FIG. 1 showing the cover pulled back to expose the applicator pad.
Figure 5:
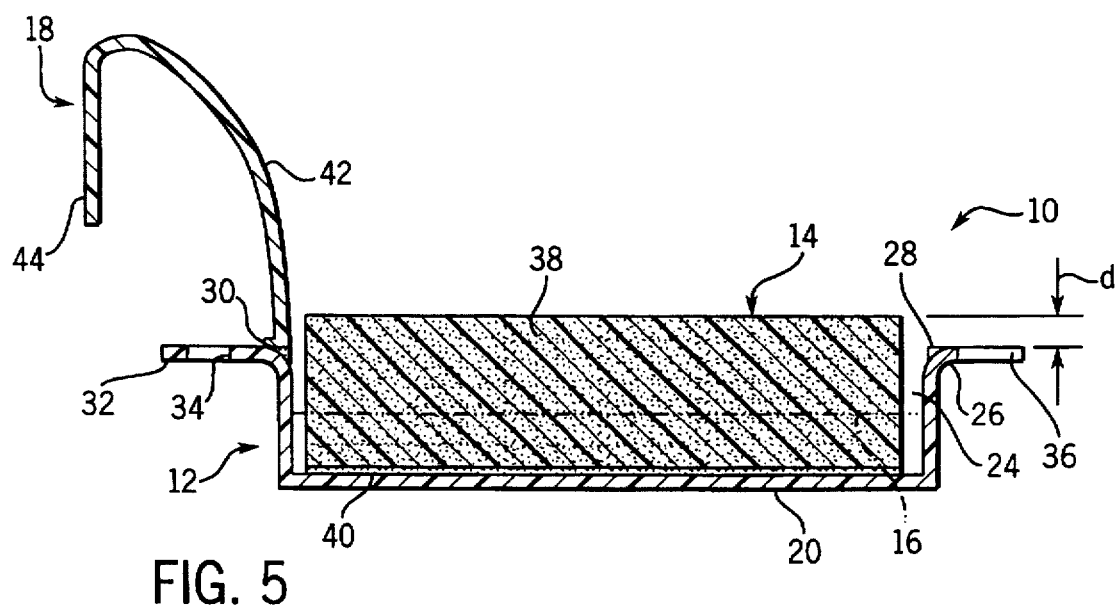
FIG. 5 is a cross-sectional view of the device taken generally along line 5—5 of FIG. 4.

Cover 18 can be designed for complete removal when it is pulled back, or it can be designed for retention to housing 12 along an edge as illustrated in FIGS. 4 and 5. Retention to housing 12 can be accomplished by providing a greater area of adhesive or heat sealing along the edge proximate tab 32. In either event, a person using device 10 simply grasps the outside of housing 12 and pulls back on cover 18 via pull tab 44 until cover 18 is separated from housing 12 a sufficient amount to expose applicator element 14 and the antiseptic or other medicinal substance. In the embodiment illustrated in FIGS. 4 and 5, applicator element 14 comprises sponge 38. Sponge 38 is slightly compressed between cover 18 and bottom wall 20 so that is extends beyond housing 12 by a desired distance d, as illustrated in FIG. 5. A child simply grasps housing 12 and rubs the extended sponge 38 and its absorbed antiseptic against the area of injury.

Figure 6:
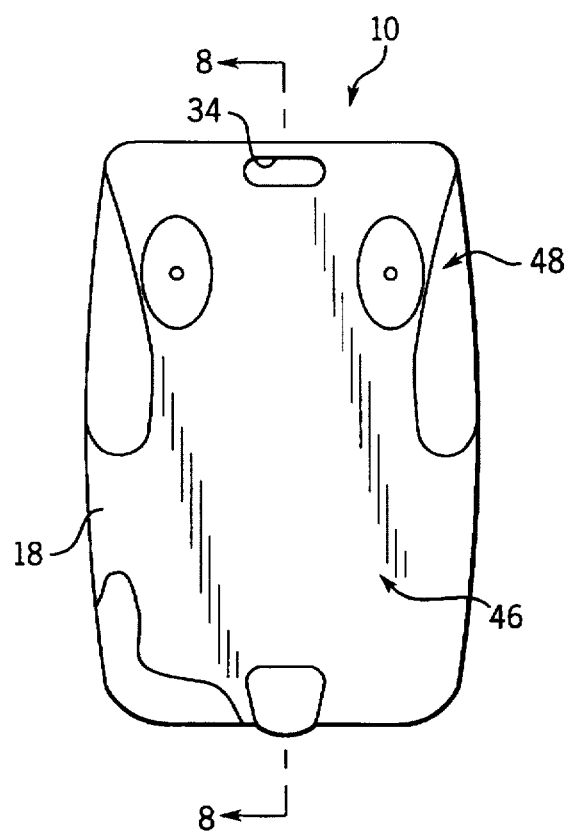
FIG. 6 is a top view of an alternate embodiment of the device illustration in FIGS. 1–5.
Figure 7:
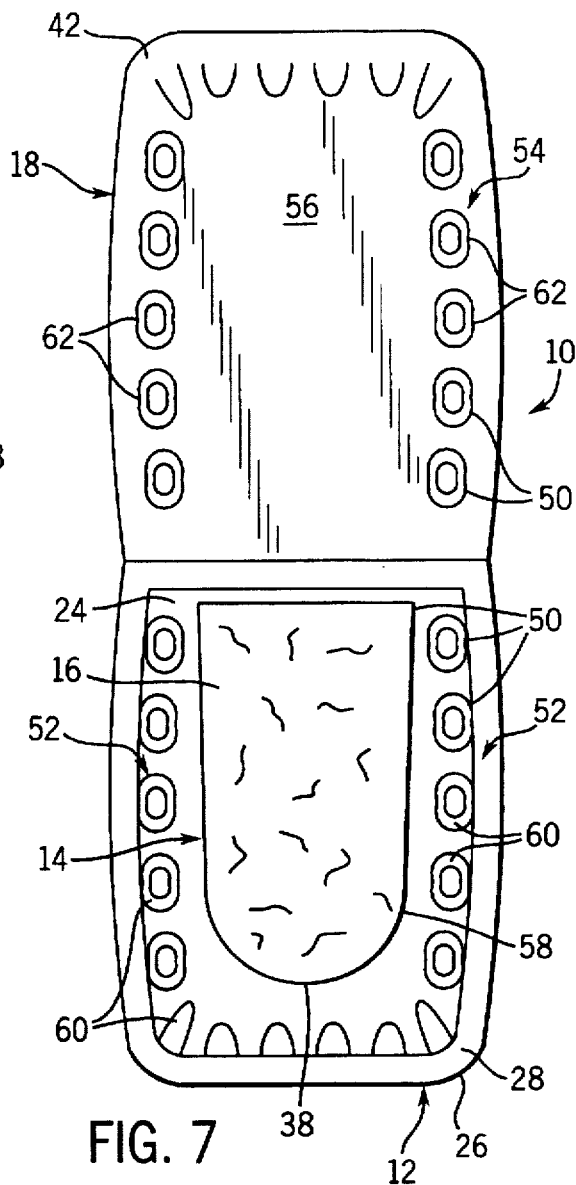
FIG. 7 is a top view of the device of FIG. 6 with the cover pulled back.
Figure 8:
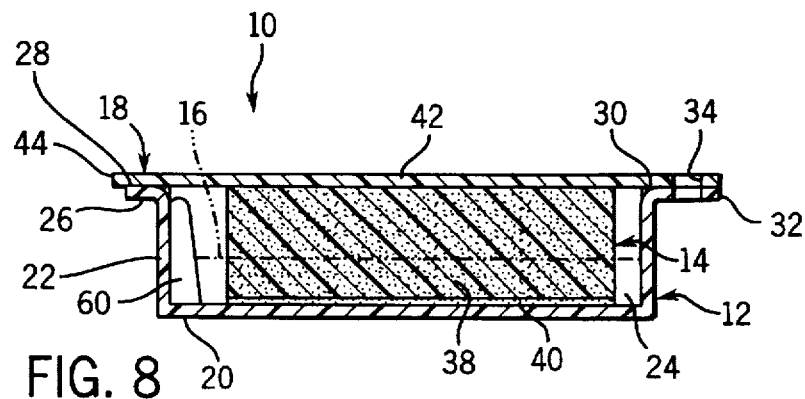
FIG. 8 is a cross-sectional view taken generally along line 8—8 of FIG. 6.

Referring generally to FIGS. 6–8, a modified embodiment of device 10 is illustrated. Many of the elements in this embodiment are common with the elements of the embodiment described with reference to FIGS. 1–5, and therefore the same reference numerals will be retained where possible to facilitate explanation.

In the embodiment of FIGS. 6–8, display area 46 typically includes a character attractive to children such as the illustrated dog's face 48. In addition to display area 46, however, this embodiment includes interior design elements 50 that may correspond to display area 46 but are visible only when cover 18 is pulled back from housing 12, as illustrated in FIG. 7. Interior design elements 50 can include several types of displays. For example, a housing display area 52 may have illustrations or other designs disposed along mounting surface 28 of rim 26. Additionally, housing display area 52 may include physical features that are attached to or molded with side wall 22 to extend into cavity 24.

An interior cover display area 54 may also be employed to provide information, illustrations, or other designs visible on an interior surface 56 of cover 18. Interior cover display area 54 preferably has a theme that corresponds both with housing display area 52 and the external display area 46. Additionally, applicator element 14, e.g., sponge 38, can include a contoured surface 58 that corresponds in some way to the information displayed at display area 46, housing display are 52 and/or interior cover display area 54.

In the illustrated embodiment, display area 46 includes dog's face 48. When cover 18 is pulled back from housing 12, it appears as though the dog is opening its mouth, because housing display area 52, interior cover display area 54 and the contoured surface of sponge 38 cooperate to provide the appearance of an inside of a dog's mouth. Specifically, housing display 52 shows the dog's bottom teeth 60 which are molded with housing 12 or displayed along rim 26. Similarly, interior cover display area illustrates the dog's upper teeth 62. To complete the theme, contoured surface 58 is contoured in the general shape of a dog's tongue and may be appropriately colored to mimic the color of a dog's tongue. Preferably, the dog's tongue, e.g. sponge 38, is slightly compressed when cover 18 is closed so that it will expand beyond rim 26 when cover 18 is pulled away from housing 12 (see the description above with respect to the embodiment illustrated in FIGS. 1–5).

By combining interesting displays in display area 46, housing display area 52 and/or interior cover display area 54, device 10 can be made to appear more interesting to children. This will encourage application of the medicinal substance 16 when necessary. Other themes can be incorporated into the various display areas instead of the dog described above. For example, contoured surface 58 may be contoured to appear as a pair of lips, a hand, or a wide variety of other designs that may be interesting to the user.

It will be understood that the foregoing description is of a preferred exemplary embodiment of this invention and that the invention is not limited to the specific forms shown. For example, the housing may be made in a variety of shapes and the applicator element may include various absorbent pads and other applicators. The cover can be constructed from a variety of materials, such as plastic, metalized film or foil. Additionally, the cover may be rigid and attached to the housing. With certain medicinal substances, it may not be necessary to entirely seal the cavity and its contents as illustrated above. These and other modifications may be made in the design and arrangement of the elements without departing from the scope of the invention as expressed in the appended claims.

What is claimed is:

1. A device for applying antiseptic to an area of injury, comprising:

a housing having a cavity and a rim extending along the periphery of the cavity;

an applicator element permanently attached to the housing and disposed within the cavity;

a cover attached to the rim to seal the applicator element within the cavity;

an antiseptic disposed within the cavity in contact with the applicator element, wherein the cover may be pulled back to expose the applicator element for use in applying the antiseptic to a desired area.

2. The device as recited in claim 1, wherein the applicator element comprises an absorbent pad.

3. The device as recited in claim 2, wherein the housing includes a bottom wall, and the absorbent pad comprises a sponge adhered to the bottom wall.

4. The device as recited in claim 1, wherein the cover includes a flexible sheet adhered to the rim.

5. The device as recited in claim 4, wherein the cover includes a pull tab to facilitate pulling the cover away from the rim.

6. The device as recited in claim 1, wherein the antiseptic comprises peroxide.

7. The device as recited in claim 1, wherein the housing includes a tab having an opening therethrough to facilitate hanging of the device on a display rack.

8. The device as recited in claim 7, wherein the housing includes a bottom wall and four side walls extending from the bottom wall to the rim.

9. The device as recited in claim 1, wherein the cover includes a display area and the housing includes a housing display area that is exposed for viewing when the cover is pulled back.

10. A device for applying antiseptic to an area of injury, comprising:

a housing having a cavity and a rim extending along the periphery of the cavity;

an applicator element attached to the housing and disposed within the cavity, the applicator element comprising an absorbent pad;

a cover attached to the rim to seal the applicator element within the cavity; and an antiseptic disposed within the cavity in contact with the applicator element, wherein the cover may be pulled back to expose the applicator element for use in applying the antiseptic to a desired area, wherein the absorbent pad is compressed when sealed within the cavity, and further wherein the absorbent pad expands and extends beyond the rim when the cover is pulled back.

11. A device for applying antiseptic to an area, comprising:

a housing having a bottom wall and a side wall extending therefrom to form a cavity, the side wall terminating in a rim opposite the bottom wall;

a pad disposed within the cavity;

an antiseptic liquid disposed within the cavity in contact with the pad; and a flexible cover sealed to the rim to retain the antiseptic liquid within the cavity prior to use, wherein the flexible cover may be pulled back to expose the pad, the pad being compressed when the flexible cover is sealed to the rim and expanded beyond the rim when the flexible cover is pulled back.

12. The device as recited in claim 11, wherein the pad comprises an absorbent sponge.

13. A device for applying antiseptic to an area, comprising:

a housing having a bottom wall and a side wall extending therefrom to form a cavity, the side wall terminating in a rim opposite the bottom wall;

a pad disposed within the cavity, the pad comprising an absorbent sponge;

an antiseptic liquid disposed within the cavity in contact with the pad; and a flexible cover sealed to the rim to retain the antiseptic liquid within the cavity prior to use, wherein the flexible cover may be pulled back to expose the pad, further wherein the absorbent sponge is permanently affixed to the housing.

14. The device as recited in claim 13, wherein the absorbent sponge is compressed when the flexible cover is sealed to the rim.

15. The device as recited in claim 13, wherein the antiseptic liquid comprises peroxide.

16. The device as recited in claim 13, wherein the flexible cover includes a display area, and the housing includes a housing display area that is exposed for viewing when the flexible cover is pulled back.

17. The device as recited in claim 13, wherein the housing includes a tab to facilitate hanging of the device for display.

18. A device for applying a medication to an area, comprising:

a housing having a cavity;

an applicator element being permanently connected to the housing and disposed in the cavity;

a medicinal substance disposed in contact with the applicator element; and a cover attached to the housing to enclose the cavity, wherein the cover can be pulled back to expose the applicator element and the medicinal substance.

19. The device as recited in claim 18, wherein the applicator element comprises an absorbent sponge.

20. The device as recited in claim 19, wherein the medicinal substance comprises an antiseptic and the cover sealingly engages the housing.

* * * * *